(12) United States Patent
Boerner et al.

(10) Patent No.: US 7,768,191 B2
(45) Date of Patent: Aug. 3, 2010

(54) ELECTROLUMINESCENT DEVICE WITH IRIDIUM COMPLEX

(75) Inventors: Herbert Friedrich Boerner, Aachen (DE); Elena Popova, Kassel (DE); Josef Salbeck, Kaufungen (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 461 days.

(21) Appl. No.: 11/816,638

(22) PCT Filed: Feb. 14, 2006

(86) PCT No.: PCT/IB2006/050474

§ 371 (c)(1), (2), (4) Date: Aug. 20, 2007

(87) PCT Pub. No.: WO2006/090301

PCT Pub. Date: Aug. 31, 2006

(65) Prior Publication Data

US 2008/0203028 A1     Aug. 28, 2008

(30) Foreign Application Priority Data

Feb. 23, 2005   (EP)   .................................. 05101350

(51) Int. Cl.
*H01J 1/62*    (2006.01)
(52) U.S. Cl. .................. 313/498; 313/503; 313/504
(58) Field of Classification Search .................. 313/498, 313/503, 504; 546/4
See application file for complete search history.

(56) References Cited

U.S. PATENT DOCUMENTS

2003/0162299 A1    8/2003   Hsieh

2004/0191959 A1    9/2004   Grushin et al.
2004/0253478 A1   12/2004   Thompson et al.
2005/0052118 A1*   3/2005   Lee et al. ..................... 313/503

(Continued)

FOREIGN PATENT DOCUMENTS

WO         0141512 A1      6/2001
WO         2005049762      6/2005

OTHER PUBLICATIONS

Lamansky S et al: "Highly Phosphorescent Bis-Cyclometalated Iridium Complexes: Synthesis, Photophysical Characterization and Use in Organic Light Emitting Diodes", Journal of the American Chemical Society,vol. 123, No. 18, pp. 4304-4312, May 9, 2001, XP002955894.

*Primary Examiner*—Ernest G Therkorn

(57) ABSTRACT

An iridium complex Ir(III)L 1L2L3 for emitting light with a central iridium ion Ir(III), with a ligand L3 as dionate from the group comprising pentane-2,4-dionate (acac), 2,2,6,6-tetramethyl-3,5-heptandionate (thd), 7,7-dimethyl-1,1,1,2,2,3,3-heptyfluoro-4,6-octandionate (fod), 4,4,4-trifluorol-(2-thienyl)butane-1,3-dionate (ttfa), 1,3-diphenylpropane-1,3-dionate (dbm), 4,4,4-trifluoro-1-(2-naphthyl)butane-1,3-dionate (tfnb) or 4,4,4-trifluoro-1-(1-naphthyl)butane-1,3-dionate and with two rigid aromatic ligands L1 and L2 with one nitrogen and one carbon atom, sharing in the ligand bond, preferably dibenzo[f,h]chinoline, benzo[h]chinoline or 5,6-dihydro-benzo[h]chinoline, characterized in that the iridium complex Ir(III)L1L2L3 is a first isomer (71), in which the nitrogen atom of the ligand L1 sharing in the ligand bonding and the nitrogen atom of the ligand L2 sharing in the ligand bonding are juxtaposed relative to the central iridium ion. The invention further relates to a method for the separation of the first isomer (71,81) of the iridium complexes (7,8) and an electroluminescent device with an electroluminescent layer (4) comprising light-emitting materials, wherein the component of the first isomer (71,81) in the total quantity of the light-emitting materials is greater than 90%, preferably greater than 95%.

2 Claims, 3 Drawing Sheets

U.S. PATENT DOCUMENTS

| | | | |
|---|---|---|---|
| 2005/0084710 A1* | 4/2005 | Kishino et al. | 428/690 |
| 2008/0030125 A1* | 2/2008 | Boerner et al. | 313/498 |
| 2008/0067925 A1* | 3/2008 | Oshiyama et al. | 313/504 |
| 2008/0191615 A1* | 8/2008 | Bechtel et al. | 313/504 |
| 2008/0203028 A1* | 8/2008 | Boerner et al. | 210/658 |
| 2009/0230841 A1* | 9/2009 | Boerner | 313/504 |

* cited by examiner

ELECTROLUMINESCENT DEVICE WITH IRIDIUM COMPLEX

REFERENCE TO RELATED APPLICATIONS

This application is a 371 of PCT/IB06/50474 filed Feb. 14, 2006.

The invention relates to an electroluminescent device with an organic light-emitting layer, light-emitting iridium complexes and a method of separating isomers from iridium complexes.

An electroluminescent device (OLED) with a layer structure consisting of a multiplicity of thin layers with an organic electroluminescent layer (EL-layer) for emitting light is known. A typical structure comprises at least a transparent electrode made of ITO (Indium Tin Oxide), an electrode made of metal and an electroluminescent layer of an organic material, arranged between the electrodes. Typically, the transparent electrode represents the anode and the metal electrode the cathode. The layer structure is deposited on a substrate that can be transparent or non-transparent depending on the direction of the light radiation. In transparent substrates the light reaches the observer through the substrate. In this case, the transparent electrode is applied to the substrate. The organic material used for the electroluminescent layer is, for example, light-emitting polymers (PLED) or small light-emitting organic molecules embedded in an organic hole- or electron-transporting matrix material. An OLED with small light-emitting molecules in the electroluminescent layer is also designated as SMOLED (Small Molecule Organic Light Emitting Diode). The electroluminescent layer has holes and electrons which meet each other and recombine. The light-emitting material is excited either directly or by energy transfer through a material-dependent electronic coupling of the light-emitting material to the matrix material. The excited light-emitting material returns to the basis state by means of light emission.

Iridium complexes Ir(III)LMN with a central iridium ion and three ligands L, M and N are known as effective light-emitting materials for SMOLEDs, owing to the use of the triplet exitones. Emission colors ranging from blue-green to red can be generated by means of variation in the ligands of the iridium complex. The concentration of the iridium complexes in the matrix material is typically 5 wt. %-11 wt. %. The wt. % unit denotes per cent by weight here. A higher concentration of the iridium complex would be desirable, but is limited due to the Dimer formation of neighboring iridium complexes and related reduction of the quantum yields due to concentration quenching. In three identical ligands L, the iridium complex Ir(III)L$_3$ can possess two isomers, one what is called facial (fac) and one meridian (mer) isomer, if besides carbon atoms, a second atom, such as nitrogen, also participates in the bonding of the ligands to the iridium atom. For example, the nitrogen atoms are arranged here in a fac-isomer in the three spatial directions with respect to the central iridium ion and in a mer-isomer in a plane with the iridium ion. In the case of Ir(III)(Phenyl pyridine)$_3$ the fac-isomer has a distinctly higher quantum yield than the mer-isomer.

The document D1 with PCT registration number PCT/IB2004/052328 unpublished as yet describes iridium complexes Ir(III)L$_2$M and Ir(III)L$_3$ with two or three rigid ligands L of dibenzo[f,h]chinoline. Rigid ligands are advantageous in respect of electrical bonding to the matrix material and show sharper emission spectra than less rigid ligands such as, for example phenyl pyridine. An iridium complex of three ligands of dibenzochinoline shows a longer wave emission at 595 nm than a preferred iridium complex with only two ligands of dibenzochinoline, such as for example Ir(dibenzochinoline)$_2$(Pentane-2,4-dionate), whose emission of 545 nm is closer to the maximum sensitivity of the human eye of 555 nm. In contrast with iridium complexes Ir(III)L$_3$ with three identical ligands, iridium complexes Ir(III)L$_2$M with two identical ligands, however, do not possess any advantageous fac/mer isometrics in respect of the quantum yield. Due to the ever falling quantum yield of the present electroluminescent compounds, there is a constant need for new electroluminescent compounds with improved light yield.

It is an object of this invention to make available an iridium complex with improved emission characteristics and improved lumen output.

This object is achieved by means of an iridium complex Ir(III)L1L2L3 for emitting light with a central iridium ion Ir(III), with a ligand L3 as dionate from the group comprising pentane-2,4-dionate (acac), 2,2,6,6-tetramethyl-3,5-heptandionate (thd), 7,7-dimethyl-1,1,1,2,2,3,3-heptyfluoro-4,6-octandionate (fod), 4,4,4-trifluorol-(2-thienyl)butane-1,3-dionate (ttfa), 1,3-diphenylpropane-1,3-dionate (dbm), 4,4,4-trifluoro-1-(2-naphthyl)butane-1,3-dionate (tfnb) or 4,4,4-trifluoro-1-(1-naphthyl)butane-1,3-dionate and with two rigid aromatic ligands L1 and L2 with one nitrogen and carbon atom, sharing in the ligand bond, each, characterized in that the iridium complex Ir(III)L1L2L3 is present as a first isomer (71,81), in which the nitrogen atom of the ligand L1 sharing in the ligand bonding and the nitrogen atom of the ligand L2 sharing in the ligand bonding are juxtaposed relative to the central iridium ion. Surprisingly, two isomers are always obtained during the synthesis of iridium complexes Ir(III)L1L2L3 with two ligands L1 and L2 as invented, a first isomer as invented and a second isomer, wherein the nitrogen atoms sharing in the ligand bonding and the central iridium ion are mutually arranged at an angle. Surprisingly, the two isomers behave very differently as light-emitting materials in a electroluminescent device even in respect of their emission characteristics. The first isomer as invented is distinguished by a quantum yield higher by a factor of more than 3.

The description rigid applies here to a ligand, in which the pyridyle ring and the phenyl ring cannot be rotated against each other. This is achieved in the ligands as invented by means of a suitable additional bridging of the pyridyle and phenyl ring. It is advantageous if the ligands are materials from the group dibenzo[f,h]chinoline, benzo[h]chinoline or 5,6-dihydro-benzo[h]chinoline. These materials are distinguished by their advantageous electronic structure, for example, an energetic high lying first triplet level. It is especially advantageous, if the iridium complex as invented possesses identical ligands L1 and L2. It is even more advantageous, if these ligands are dibenzo[f,h]chinoline. These ligands have a greater aromatic system than, for example, benzo[h]chinoline and therefore have a distinctly better transportability for charges.

It is especially advantageous if the iridium complex has, as ligand L3, pentane-2,4-dionate, (also designated below as "acac") or 2,2,6,6-tetramethyl-3,5-heptandionate (thd) with good complexing characteristics.

Furthermore, the invention relates to an electroluminescent device with an organic electroluminescent layer comprising a light-emitting material, which has a component of a first isomer (71,81) of an iridium complex, as claimed in Claim 1 higher, than 90%, preferably higher than 95%, in relation to the total quantity of the light-emitting material. Typical synthesis methods provide iridium complexes from a mixture of first and second isomers with a component of the second isomer in the total quantity of the iridium complexes between 17% and 20%. In the event of a reduction in the component of the second isomer to 10% or 5%, as the case may be, the quantum yield of the electroluminescent layer rises by 6% to 9% or 10% to 13%, respectively. If 100% of the light-emitting material is made up of the first isomer of the iridium complex as invented, the rise in the quantum yield can be even 15% to 17%.

It is especially advantageous for an efficient excitation of the light-emitting materials, if the light-emitting material is embedded in a hole and electron-conducting matrix material and the first isomers (71,81) of an iridium complexes possess a weight component between 1 wt. % and 50 wt. % relative to the matrix material, preferably between 2 wt. % and 12 wt. %. The wt. % unit denotes percent by weight.

Furthermore, the invention relates to a method for the separation of the first isomer of the iridium complex as invented as claimed in Claim 1 from a quantity of iridium complexes that contains a second isomer in addition to the first isomer as invented, in which second isomer the nitrogen atoms of the ligands L1 and L2 lie in one plane with the central iridium-ion, which method comprises the steps of filling a quantity of iridium complexes of first and second isomers in a column chromatograph with a fixed phase, preferably $SiO_2$, separating the first and second isomers in the column chromatograph with suitable column length by means of an elution medium, preferably dichloromethane/hexane/ether in the ratio 4:1:0.2, collecting the solution from elution medium in the first and second isomer in various ratios as a function of the separation time in column chromatographs, determining the ratio between first and second isomers by using thin layer chromatography based on the isomer-specific Rf-values, where the first isomer has a greater Rf value than the second isomer, and repeating the sequence from step 1 for the collected material in the various containers with a component of the second isomer in the total quantity of the iridium complex above a threshold value, which is preferably lower than or equal to 1%. The ratio of the section of the investigated substance to the section of the mobile phase is designated as the Rf value in thin layer chromatography.

The method for the separation of the first isomer is especially advantageous, if a mobile phase of ethyl acetate/hexane is used in the ratio 2:1 in the thin layer chromatography for determining the relation between the first (71,81) and the second isomer (72,82), where the first isomer (71,81) has an Rf value of 0.81 and the second isomer (72,82) an Rf value of 0.72.

These and other aspects of the invention are apparent from and will be elucidated, by way of non-limitative example, with reference to the embodiment(s) described hereinafter.

DESCRIPTION OF THE PREFERRED EMBODIMENTS

Figure 1:
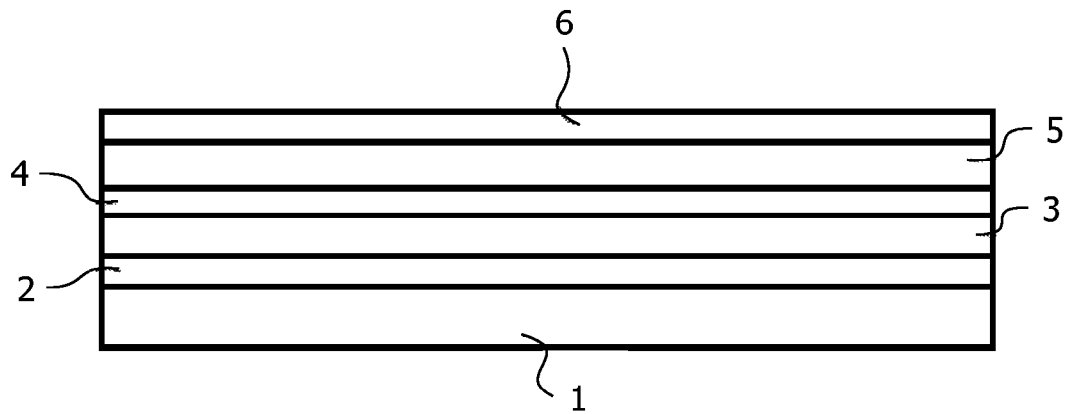
FIG. 1: shows an electroluminescent device in cross section.

FIG. 1 shows an electroluminescent device that has a substrate 1 and deposited on it at least an anode 2, an electroluminescent layer 4 and a cathode 6. To improve the efficiency of an electroluminescent device, it can have, as shown in FIG. 1, an additional hole-transporting layer 3 between anode 2 and electroluminescent layer 4 as well as an electron-transporting layer 5 between cathode 6 and electroluminescent layer 4. Depending on the desired light exit direction through the substrate (bottom-emitter) or on the side facing away from the substrate (top-emitter), the layer structure can also be arranged in reverse order.

In the case of bottom-emitters, the substrate 1 is preferably a transparent glass plate or a transparent plastic plate. The plastic plate can contain, for example, polyethyletherephtalate (PET). The anode 2 is preferably transparent and can contain, for example, p-doped silicon, indium-doped tin oxide (ITO) or antimony doped tin oxide (ATO). The anode preferably contains 2 ITO. The anode 2 is not structured, but is executed as a surface. The cathode 6 can contain a metal such as aluminum, copper, silver or gold, an alloy or n-doped silicon. The cathode 6 can preferably also have two or more conductive layers. It can be especially preferred that the cathode 6 contain a first layer of a base metal, such as for example calcium, barium or LiF and a second layer of aluminum. The cathode 6 can be structured and for example contain a multiplicity of parallel strips of the conductive material(s). Alternatively, the cathode 6 can be unstructured and can be executed as a surface. The anode 2 borders on a first hole-transport layer 3, which in preferred embodiments comprises a hole injection layer made of, for example, 4.4',4"-tris-(N-(3-methyl-phenyl)-N-phenylamino)-triphenylamine (MT-DATA) with a 1% doping with tetrafluoro-tetracyano-quinodimethane (F4-TCNQ) and a hole transport layer of, for example, triarylamines, diarylamines, tristilbenamines or a mixture of polyethylene dioxythiophene (PDOT) and poly (styrene sulfonate).

A hole-blocking and electron-transporting layer 5, which can contain, for example, tri-(8-hydroxy-chinolato)-aluminum (Alq$_3$), 1,3,5-tri-(1-phenyl-1H-benzimidazole-2-yl) benzol (TPBI) or low-electron heterocyclics such as 1,3,4-oxadiazoles or 1,2,4-triazole, is disposed between cathode 6 and electroluminescent layer 4.

The electroluminescent layer 4 comprises, as invented, first isomers 71, 81 of the iridium complex as a light-emitting material. The iridium complexes can then be used alone (100 wt. % in relation to the total weight of the light-emitting layer 4) or embedded in a matrix of a hole- or electron-transporting material in the light-emitting layer 4. Preferably the quantity of iridium complexes is between 1 wt. % and 50 wt. %, especially preferably between 2 wt. % and 12 wt. %, in relation to the total weight of the light-emitting layer 4 of matrix material and light-emitting material. The selection of the matrix material depends on the requirements of the iridium complex. For example, the matrix may comprise 4.4', 4"-tri(N-carbazolyl) triphenylamine (TCTA), 2,9-dimethyl-4,7-diphenyl-1,10-phenanthroline (BCP) or 1,3,5-tri-(1-phenyl-1H-benzimidazole-2-yl)benzol (TPBI) or N,N-diphenyl-N,N-di-(3-methyl-phenyl)-Benzedrine (TPD).

The light-emitting iridium complex as invented is distinguished by the ligand bonding between the central iridium ion and the three ligands L1, L2 and L3. The ligands L1 and L2 each contain a nitrogen atom and a carbon atom which share in the ligand bonding. The iridium complexes as invented are distinguished in that the nitrogen atoms sharing in the ligand bonding are mutually juxtaposed in relation to the central iridium ion. The ligands L1 and L2 can additionally have other substituents R, which influence the electronic characteristics of the ligands and thus also of the later iridium complexes. Especially preferable examples for L1 and L2 are dibenzo[f,h]chinoline, benzo[h]chinoline and/or 5,6-dihydro-benzo[h]chinoline, which can have one or more substituents R1, R2 and/or R3:

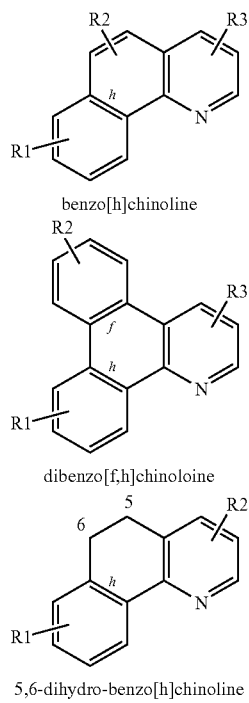

benzo[h]chinoline dibenzo[f,h]chinoloine 5,6-dihydro-benzo[h]chinoline

The substituents R1, R2, R3, etc. can contain, for example, linear or branched $C_1$-$C_8$-alkyl groups, $C_2$-$C_6$-alkenyl groups, $C_3$-$C_8$-cycloalkyl groups, $C_1$-$C_6$-alkinyl groups, aryl groups, heteroaryl groups, $C_1$-$C_6$-heterocycloalkyl groups, amines, phosphates, phosphine groups, phosphine oxide groups, halogens, sulfate groups, sulfonate groups, sulfon groups, carboxylates, $C_2$-$C_6$-alkoxy groups, phosphate groups etc. The substituents R1, R2, R3, can be the same or different.

The ligand L3 with complexing characteristics is an anion from the group of the dionates:

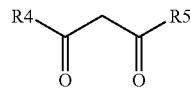

The substituents R4 and R5 can contain, for example, linear or branched $C_1$-$C_8$-alkyl groups, $C_2$-$C_6$-alkenyl groups, $C_3$-$C_8$-cycloalkyl groups, $C_1$-$C_6$-alkinyl groups, aryl groups, heteroaryl groups, $C_1$-$C_6$-heterocycloalkyl groups, amine, phosphates, phosphine groups, phosphine oxide groups, halogens, sulfate groups, sulfonate groups, sulfon groups, carboxylates, $C_2$-$C_6$-alkoxy groups, phosphate groups etc. The substituents $R_4$ and $R_5$, can be the same or different.

Preferably, the third ligand L3 is selected from the group of pentane-2,4-dionate (acac), 2,2,6,6-tetramethyl-3,5-heptandionate (thd), 7,7-dimethyl-1,1,1,2,2,3,3-heptafluoro-4,6-octandionate (fod), 4,4,4-trifluoro-1-(2-thienyl)butane-1,3-dionate (ttfa), 1,3 diphenylpropane-1,3-dionate (dbm), 4,4,4-trifluoro-1-(2-naphthyl)butane-1,3-dionate (tfnb) and 4,4,4-trifluoro-1-(1-napthyl)butane-1,3-dionate. These are all known and well-complexing ligands. A quite preferred ligand is pentane-2,4-dionate (acac).

Figure 2:
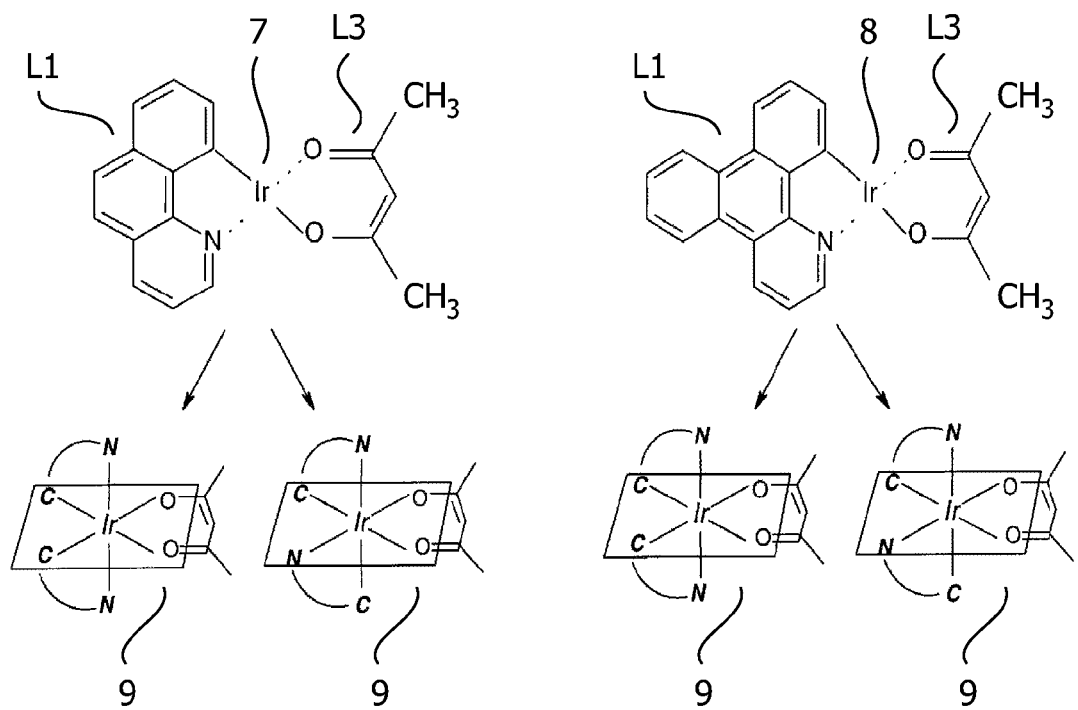
FIG. 2: shows a spatial bonding pattern of the first and second isomers of Ir-(benzo[h]chinoline)$_2$(acac) and Ir-(dibenzo[f,h]chinoline)$_2$(acac)

FIG. 2 shows by way of example two different iridium complexes 7 and 8 in a top view, wherein only two ligands L1 and L3 are shown each (Ir-(benzo[h]chinoline)$_2$(acac) referred to as 7 and Ir-(dibenzo[f,h]chinoline)$_2$(acac) referred to as 8). FIG. 2 shows 7 benzo[h]chinoline as ligand L1 of the iridium complex, 8 dibenzo[f,h]chinoline as ligand L1 of the iridium complex. These Ir-complexes possess two isomers, first isomers 71 and 81 and second isomers 72 and 82, whose spatial bonding patterns are shown in FIG. 2, 71 and 72 for Ir-(benzo[h]chinoline)$_2$(acac) and 81 and 82 for Ir-(dibenzo[f,h]chinoline)$_2$(acac). The ligand L3 of the iridium complexes 7 and 8 is a ligand from the group of the dionates, in this example pentane-2,4-dionate (acac). The spatial position of the ligands is indicated by the respective arcs, which connect the corresponding nitrogen-carbon pairs of the ligands. The first isomer as invented differs from the second isomer by the position of the nitrogen atoms (N) relative to the iridium atoms sharing in the ligand bonding. In the case of the first isomers 71 and 81 as invented the nitrogen atoms (N) lie on the opposing sides of the central iridium ions (called trans-position), while the carbon atoms (C) sharing in the iridium complex bond lie next to each other in relation to the iridium atom (called cis-position). The nitrogen atoms thus lie outside the plane 9, which is spanned by the hydrogen atoms of the ligand L3 and by the central iridium ion. The nitrogen atoms sharing in the iridium complex bond as well as the carbon atoms sharing in the iridium complex bond occupy neighboring cis-positions in the second isomers 72 and 82 shown in FIG. 2. Here, there is one nitrogen and one carbon atom each in the plane 9. The first isomers 71 and 81 as invented are therefore distinguished by a (C-cis, N-trans)-geometry, while the second isomers 72 and 82 have a (C-cis, N-cis)-geometry. The ligands L1 and L2 shown in FIG. 2 for example can have even additional substituents R1, R2 and/or R3 in other embodiments.

The invention, however, also comprises first isomers of iridium complexes with other rigid ligands, which similarly have a ligand bonding schematically shown in FIG. 2 with a (C-cis, N-trans)-geometry relative to the central iridium ion. Even here, the ligands can contain one or more substituents R1, R2, R3. The substituents R1, R2, R3, etc. can contain, for example, linear or branched $C_1$-$C_8$-alkyl groups, $C_2$-$C_6$-alkenyl groups, $C_3$-$C_8$-cycloalkyl groups, $C_1$-$C_6$-alkinyl groups, aryl groups, heteroaryl groups, $C_1$-$C_6$-heterocycloalkyl groups, amines, phosphates, phosphine groups, phosphine oxide groups, halogens, sulfate groups, sulfonate groups, sulfon groups, carboxylates, $C_2$-$C_6$-alkoxy groups, phosphate groups etc.

Figure 3:
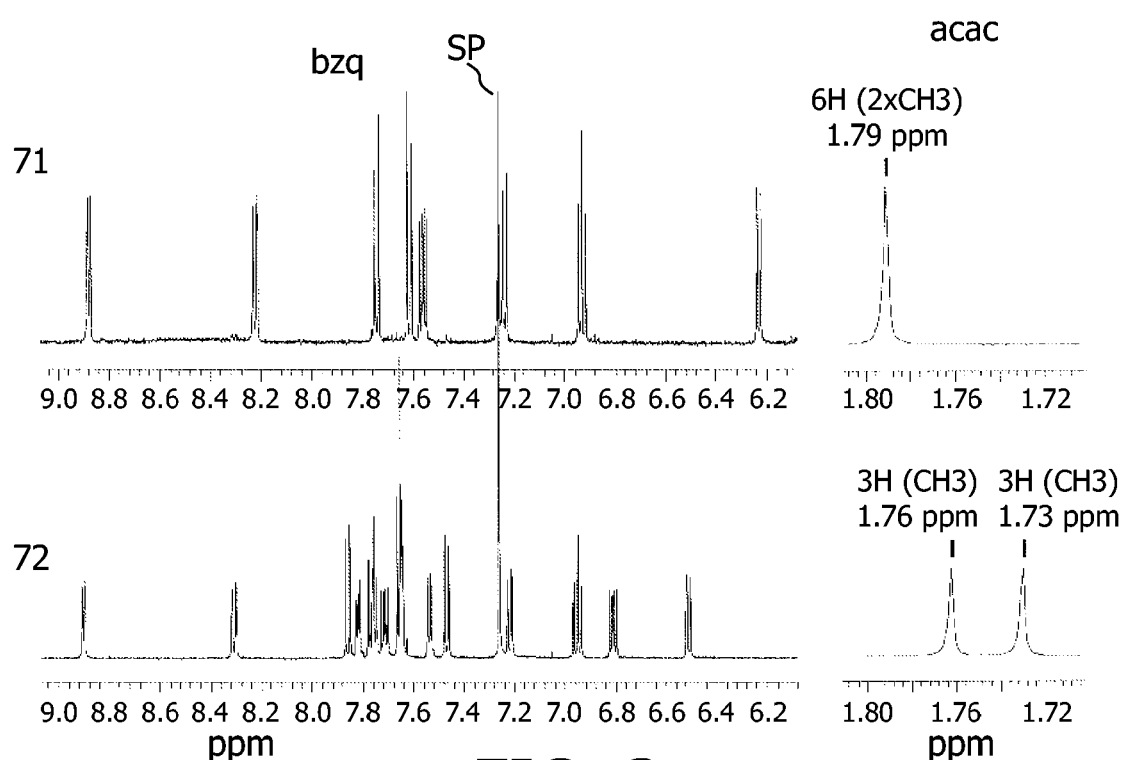
FIG. 3: shows $^1$H NMR spectra of the first and second isomers of Ir-(benzo[h] chinoline)$_2$(acac)
Figure 4:
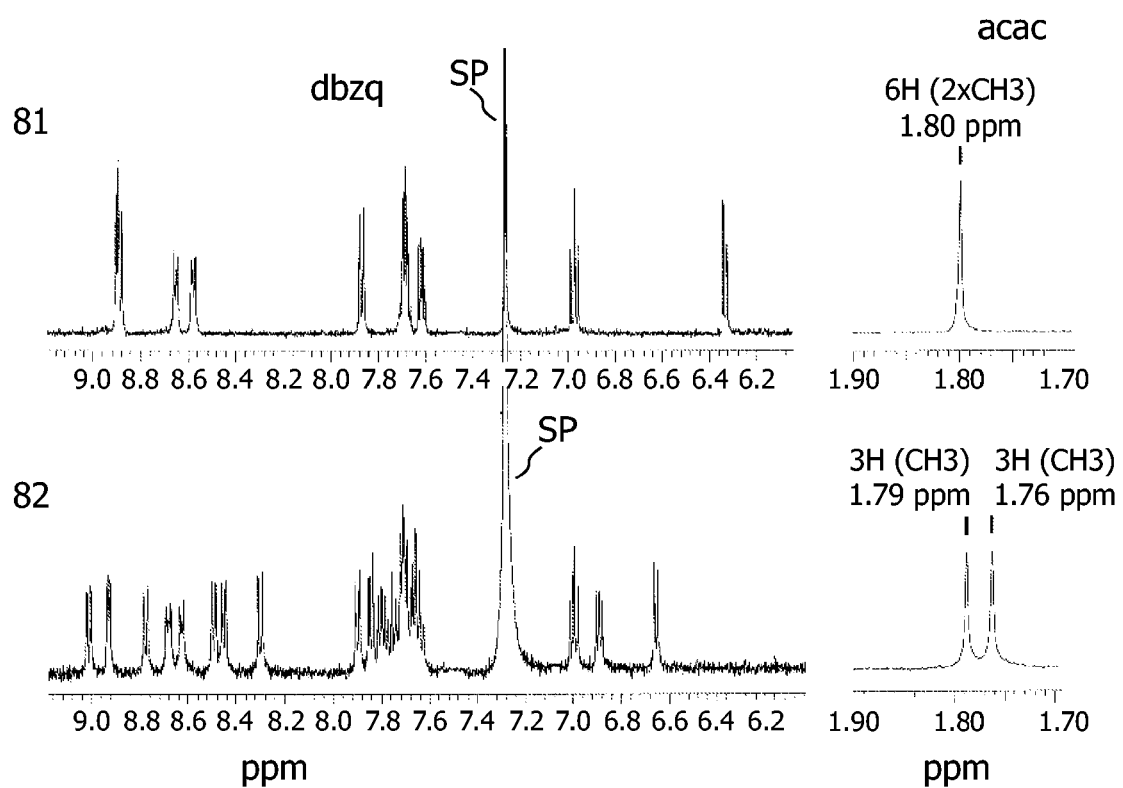
FIG. 4: shows $^1$H NMR spectra of the first and second isomers of Ir-(dibenzo[f,h]chinoline)$_2$(acac)

First isomers 71 and 81 and second isomers 72 and 82 can be differentiated by means of $^1$H NMR spectra of iridium complexes, dissolved in CDCl3, as is shown in FIG. 3 for example, for Ir-(benzo[h]chinoline)$_2$(acac) 71 and 72 (on the left hand side benzo[h]chinoline (designated as bzq), on the right hand side acac) and in FIG. 4 for example, for Ir-(dibenzo[f,h]chinoline)$_2$(acac) 81 and 82 (on the left hand side dibenzo[f,h]chinoline (designated as dbzq), on the right hand side acac). FIGS. 3 and 4 show lines designated as SP in the spectra corresponding to the line of the solvent carbon deuterium chloride (CDCl3). The first isomers show distinctly fewer spectral lines than the second isomers in the case of (bzq) in the range from 6.7 ppm to 7.0 ppm and in the range from 7.4 ppm to 8.0 ppm as well as also in the case of (dbzq) in the range from 6.6 ppm to 7.1 ppm and in the range from 7.5 ppm to 9.2 ppm. Similarly, the signals for the third ligands L3 show distinct differences between the first and the second isomer. In the respective second isomers, the (acac)-spectrum has a characteristic splitting, which is not present in the case of the first isomers.

The spectroscopic data in detail for the first isomers of the iridium complexes Ir-(benzo[h]chinoline)$_2$(acac) 71 and Ir-(dibenzo[f,h]chinoline)$_2$(acac) 81, as invented, are: 71) δ(CDCl3, ppm): 8.88 (d, J=5.4 Hz, 2H), 8.22 (d, J=7.8 Hz, 2H), 7.74 (d, J=8.8 Hz, 2H), 7.61 (d, J=8.8 Hz, 2H), 7.56 (dd, J=8.4, J=5.4 Hz, 2H), 7.24 (d, J=7.8 Hz, 2H), 6.93 (t, J=7.5 Hz, 2H), 6.23 (d, J=7.2 Hz, 2H), 5.28 (s, 1H), 1.79 (s, 6H, 2CH3); 81) δ(CDCl3, ppm): $S_H$=8.87-8.91 (m, 4H), 8.64-8.68 (m, 2H), 8.56-8.60 (m, 2H), 7.87 (d, J=7.9 Hz, 2H), 7.66-7.71 (m, 4H), 7.61 (dd, J=7.8 Hz, J=5.4 Hz, 2H), 6.97 (t, J=7.9 Hz, 2H), 6.33 (d, J=7.3 Hz, 2H), 5.29 (s, 1H), 1.80 (s, 6H, 2CH$_3$);

By using X-ray crystallography it has turned out that the respective lengths of the two N—Ir bonds in the first isomer and the two Ir—O bonds are equal, whereas the lengths of the two N—Ir-bonds and the two Ir—O— bonds in the second isomer are distinctly different, which is particularly noticeable from the spectral differences.

The quantum yield of the first isomer is surprisingly distinctly higher than that of the second isomer, for example, by the factors 3.83 and 3.76 for Ir-(benzo[h]chinoline)$_2$(acac) and Ir-(dibenzo[f,h]chinoline)$_2$(acac). Comparative investigations on other iridium complexes have shown that the advantageous effect of the first isomer occurs only for rigid ligands, though even other less rigid iridium complexes such as, for example, Ir-(phenylpyridine)$_2$(acac) have these isometrics. The description rigid applies here to a ligand, in which the pyridyle ring and the phenyl ring cannot be rotated against each other. This is achieved in the ligands as invented by means of a suitable additional bridging of the pyridyle and phenyl ring.

Figure 5:
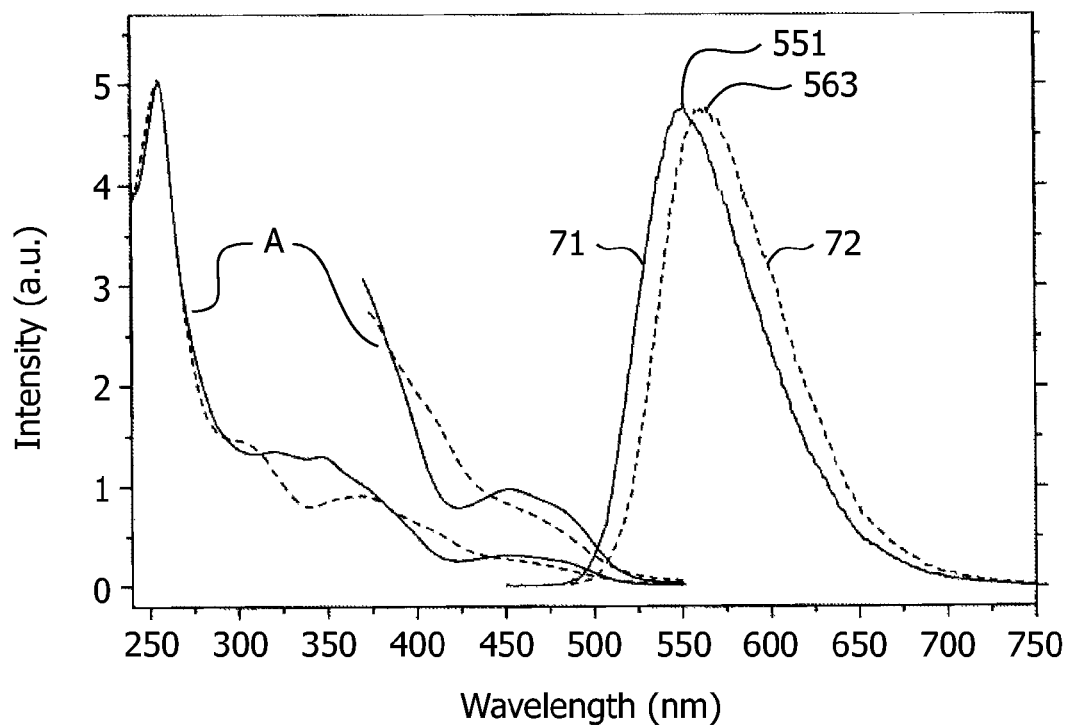
FIGS. 5 and 6: show absorption—(A) and emission spectra of Ir-(benzo[h]chinoline)$_2$(acac) and Ir-(dibenzo[f,h]chinoline)$_2$(acac) for the respective first and second isomers.

FIG. 5 shows the emission spectra of first 71 and second 72 isomers of the Ir-(benzo[h]chinoline)$_2$(acac)-complex in any units as a function of the wavelength at room temperature, dissolved in CH$_2$Cl$_2$. The maximum of the emission for Ir-(benzo[h]chinoline)$_2$(acac) is in the range from 551 nm-563 nm, wherein the maximum of the emission of the first isomer 71 at 551 nm is shifted by 12 nm as against the second isomer to shorter wavelengths. The spectral lines designated A are absorption lines. The two isomers scarcely differ from each other, because the absorption is dominated by the ligand type and thus predominantly insensitive to isomers.

Figure 6:
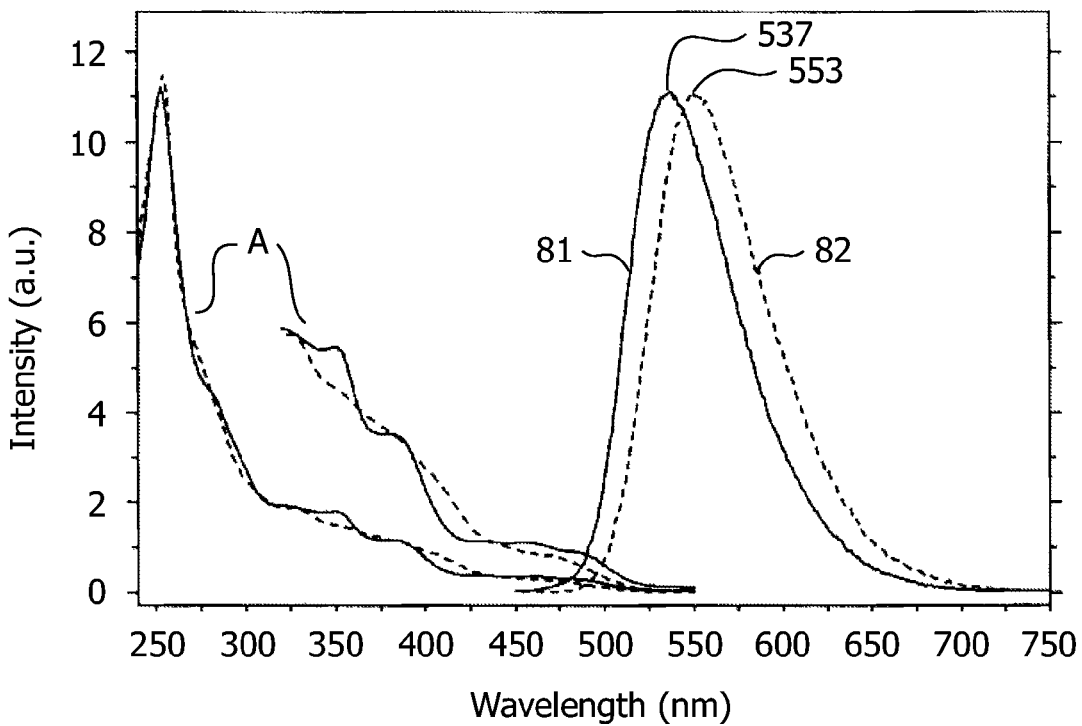

FIG. 6 shows the emission spectra of first 81 and second 82 isomers of the Ir-(dibenzo[h]chinoline)$_2$(acac)-complex in any units as a function of the wavelength at room temperature, dissolved in CH$_2$Cl$_2$. The maximum of the emission is in the range from 537 nm-553 nm for Ir-(dibenzo[h]chinoline)$_2$ (acac), wherein the maxima of the emission of the first isomer 81 at 537 nm is shifted by 16 nm as against the second isomer to shorter wavelengths. Further it also turns out that the emission is also dependent on the size of the ligands, as can be seen in the comparison of the FIGS. 5 and 6. The spectral lines designated A are absorption lines. The two isomers scarcely differ from each other here, because the absorption is dominated by the ligand type and is thus predominantly insensitive to isomers.

A known synthesis method for iridium complexes is, for example, the manufacture of the Ir-(dibenzo[f,h]chinoline)$_2$ (acac) through the dichloro-bridged dimer (dibenzochinoline)$_2$Ir(μ-Cl)$_2$(dibenzochinoline)$_2$ as intermediate product. A solution of 0.40 g of dibenzochinoline (dbzq) is prepared here in 15 ml 2-ethoxyethanol in a nitrogen atmosphere. Thereafter, add 5 ml water and Ir(III)-chlorohydrate and heat for 24 h with return flow. The yellow precipitate obtained on cooling to room temperature is centrifuged and subjected to multiple washing with methanol. 0.47 g of the dichloro-bridged dimer (dbzq)$_2$Ir(μ-Cl)$_2$(dbzq)$_2$ is dissolved in 10 ml of 2-ethoxyethanol in nitrogen atmosphere, 0.25 g of sodium carbonate and 0.12 ml of acetyl acetonate (acac) added to the solution and the solution heated at 100° C. for 10 hrs with return flow. Water is then added, the yellow precipitate obtained is centrifuged and subjected to multiple washing with methanol. Then the precipitate is dried in vacuum. In this method, Ir-(dibenzo[f,h]chinoline)$_2$(acac) complex is obtained as a mixture of first and second isomer at a ratio of 4:1. A variation of the synthesis conditions such as time and temperature has only a minor effect on the isomer ratio. Other known synthesis methods for manufacturing iridium complexes provide similar results in terms of the isomer ratio.

The relative component of the second isomer rises on expansion of the ligands L1,L2; correspondingly syntheses with smaller ligands yield more advantageous ratios, for example Ir-(benzo[h]chinoline)$_2$(acac) yields a ratio of first to second isomer of 5:1. Due to the better loading transport characteristics, however, bigger ligands are to be preferred for electroluminescent devices.

To achieve improvement in the quantum yields by using an improved light-emitting material, the first and second isomers must first be insulated from each other. In the case of a quantum yield of the first isomer higher by a factor of 3.8, the quantum yield of an electroluminescent layer with a component of the first isomer of greater than 90% in the total quantity of the iridium complexes can be increased by at least 9% and with a component of 95% in the total quantity of the iridium complexes by at least 13% compared to light-emitting iridium complexes without carrying out isomer separation. If 100% of the light-emitting material is made up of the first isomer of the iridium complex as invented, the rise in the quantum yield can be even 17%.

A separation of the two isomers for manufacturing iridium complexes from exclusively the first isomer is made possible by the invented separation method by means of columnar chromatography. The two isomers differ from each other, among other things, by what are called Rf values. The ratio of the propagation of the substance to be investigated to the propagation of the mobile phase, for example an aqueous solution of butanol or phenol, is plotted on a suitable paper as Rf-value (or also designated as relate-to-front) in thin layer chromatography.

For this purpose, a quantity of material from iridium complexes from first and second isomers is separated into first and second isomers by using column chromatography with suitable column lengths. The method comprises, as steps, filling up a quantity of iridium complexes into a column chromatograph with solid phase, preferably SiO$_2$, separation of the first and second isomers in the column chromatograph by using an elution medium, preferably dichloromethane/hexane/ether in the ratio 4:1:0.2, wherein the first isomer has a higher Rf value than the second isomer, collection of the solution of elution medium with first and/or second isomers into various repositories as a function of the separation period in the column chromatograph, determination of the quantity ratio between first and second isomers by means of thin layer chromatography using the isomer-specific Rf values, for example with ethylacetate (EtOAc)/hexane 2:1 as a mobile phase, of 0.81 for the first isomer and 0.72 for the second isomer and repetition of the process from the first step for the collected material in the various repositories, which have a proportion of the second isomer above a threshold value, preferably lower than or equal to 1%. Already after the first chromatographic cycle, 70% of the first isomer is obtained in pure form. The Rf values of the first and second isomers are predominantly dependent on the choice of the ligand.

An example of embodiment for an electroluminescent device as invented:

Glass substrate with a 150 nm thick anode made of Indium tin oxide (ITO)

Hole injection layer of MTDATA with 1% F4-TCNQ, thickness 400 nm

Hole transport layer of MTDATA, undoped, thickness 100 nm

Emission layer of TPD, with 9 wt. % iridium complexes as invented of 100% first isomers, thickness 150 nm Hole blockade- and electron transport layer of TPBI, thickness 500 nm Electron injection layer of LiF, thickness 1 nm Cathode of aluminum, thickness 70 nm The electroluminescent layer (emission layer) can also additionally contain, besides the iridium complexes as invented, other light-emitting materials, for example, for generating colored light, especially white light.

The embodiments explained with the help of figures and the description represent only examples for improvement in the emission characteristics and lumen output of an electroluminescent device and should not be understood as restrictive on the patent claims to these examples. Even alternative embodiments are possible for the expert, which are also covered by the scope of protection of the patent claims. The numbering of the independent claims should not imply that other combinations of the claims do not represent advantageous embodiments of the invention.

The invention claimed is:

1. An electroluminescent device with an organic electroluminescent layer comprising a light-emitting material including a first isomer of an iridium complex in a quantity higher than 90%, in relation to the total quantity of the light-emitting material, wherein the iridium complex comprises an iridium complex Ir(III)L1L2L3 for emitting light with a central iridium ion Ir(III), with a ligand L3 as a dionate selected from the group consisting of: pentane-2,4-dionate (acac), 2,2,6,6-tetramethyl-3,5-heptandionate (thd), 7,7-dimethy-1,1,1,2,2,3,3-heptyfluoro-4,6-octandionate (fod), 4,4,4-trifluorol-(2-thienyl)butane-1,3-dionate (ttfa), 1,3-diphenylpropane-1,3-dionate (dbm), 4,4,4-trifluoro-1-(2-naphthyl)butane-1,3-dionate (tfnb) or 4,4,4-trifluoro-1-(1-naphthyl)butane-1,3-dionate and with two rigid aromatic ligands L1 and L2 with one nitrogen and carbon atom, sharing in the ligand bond, each, wherein the iridium complex Ir(III)L1L2L3 is present as a first isomer, in which the nitrogen atom of the ligand L1 sharing in the ligand bonding and the nitrogen atom of the ligand L2 sharing in the ligand bonding are juxtaposed relative to the central iridium ion, wherein L1 an L2 are dibenzo[f,h] chinoline and L3 is pentane-2,4-dionate (acac).

2. An electroluminescent device as claimed in claim 1, wherein light-emitting material is embedded in a hole- and electron-conducting matrix material, wherein the first isomers (71,81) of an iridium complex have a weight component between 1 wt. % and 50 wt. % relative to the matrix material.

* * * * *